(12) United States Patent
Geist

(10) Patent No.: US 10,687,845 B2
(45) Date of Patent: Jun. 23, 2020

(54) TRAJECTORY GUIDANCE DEVICE AND SYSTEM FOR SURGICAL INSTRUMENTS

(71) Applicant: Integrity Implants, Inc., Cooper City, FL (US)

(72) Inventor: Wyatt Drake Geist, Davie, FL (US)

(73) Assignee: Integrity Implants Inc., Cooper City, FL (US)

(*) Notice: Subject to any disclaimer, the term of this patent is extended or adjusted under 35 U.S.C. 154(b) by 798 days.

(21) Appl. No.: 15/313,463

(22) PCT Filed: May 22, 2015

(86) PCT No.: PCT/US2015/032235
§ 371 (c)(1),
(2) Date: Nov. 22, 2016

(87) PCT Pub. No.: WO2015/183747
PCT Pub. Date: Dec. 3, 2015

(65) Prior Publication Data
US 2017/0189058 A1    Jul. 6, 2017

Related U.S. Application Data

(60) Provisional application No. 62/002,734, filed on May 23, 2014, provisional application No. 62/059,455, filed on Oct. 3, 2014.

(51) Int. Cl.
*A61B 17/58* (2006.01)
*A61B 17/60* (2006.01)
(Continued)

(52) U.S. Cl.
CPC ............ *A61B 17/3403* (2013.01); *A61B 6/12* (2013.01); *A61B 10/025* (2013.01); *A61B 17/3472* (2013.01); *A61B 90/11* (2016.02); *A61B 2010/0258* (2013.01); *A61B 2090/376* (2016.02); *A61B 2090/3966* (2016.02)

(58) Field of Classification Search
CPC combination set(s) only.
See application file for complete search history.

(56) References Cited

U.S. PATENT DOCUMENTS

| 6,428,547 B1 | 8/2002 | Vilsmeier et al. |
| 2006/0085072 A1* | 4/2006 | Funk ............... A61F 2/4405 623/17.11 |
| 2012/0253353 A1 | 10/2012 | McBride |

FOREIGN PATENT DOCUMENTS

WO    WO2014005225    1/2014

* cited by examiner

*Primary Examiner* — Sameh R Boles
(74) *Attorney, Agent, or Firm* — McHale & Slavin, P.A.

(57) ABSTRACT

The invention relates to a trajectory guidance instrument that is securable to a surgical tool for use in conjunction with X-ray machines. More particularly, the device includes a radiolucent outrigger having radiodense indicia disposed on the outrigger so that the radiodense indicia is visible via an X-ray machine to provide an angular trajectory for the instrument. The outrigger is securable to various surgical tools for the purpose of providing real time trajectory guidance to surgeons during a procedure. In general, the precision trajectory guidance instrument comprises a substantially rigid outrigger device which it securable to a portion of the surgical tool for trajectory guidance. The trajectory guidance instrument may be attached with clips, fasteners, adhesives, hook and loop or the like.

28 Claims, 18 Drawing Sheets

(51) Int. Cl.
*A61F 2/00* (2006.01)
*A61B 17/34* (2006.01)
*A61B 10/02* (2006.01)
*A61B 90/11* (2016.01)
*A61B 6/12* (2006.01)
*A61B 90/00* (2016.01)

TRAJECTORY GUIDANCE DEVICE AND SYSTEM FOR SURGICAL INSTRUMENTS

CROSS REFERENCE TO RELATED APPLICATIONS

This is a national stage filing in accordance with 35 U.S.C. § 371 of PCT/US2015/032235, filed May 22, 2015, which claims the benefit of the priority of U.S. Provisional Patent Application No. 62/002,734, entitled "TRAJECTORY AND DEPTH GUIDANCE INSTRUMENT", filed May 23, 2014, and U.S. Provisional Patent Application No. 62/059,455, entitled "TRAJECTORY GUIDANCE DEVICE AND SYSTEM FOR SURGICAL INSTRUMENTS", filed Oct. 3, 2014. The contents of each of the above referenced applications are incorporated herein by reference.

FIELD OF THE INVENTION

The invention relates to a trajectory guidance instrument that is securable to a surgical tool for use in conjunction with X-ray machines. In particular, the device includes a radiolucent outrigger having radiodense indicia disposed on the outrigger that is visible via the X-ray machine to provide an angular trajectory for the instrument.

BACKGROUND

Medical procedures involving the vertebrae are normally complicated because of the preciseness and accuracy required to avoid both neural damage and injury to major blood vessels. Precision depth guided instruments are required to perform percutaneous spinal surgery. These surgeries sometimes require penetration of the hard cortical bone of the vertebra and traversal of the softer cancellous bone lying thereunder. A large force is normally required by the surgeon to penetrate the cortical bone. Once the cortical bone is penetrated, extreme care must then be taken to avoid rapidly penetrating through all of the cancellous bone. There is also the danger of rapidly passing through the cancellous bone and then through the cortical bone on the other side of the vertebra. This can result in injury or damage to the spinal cord and/or other organs or blood vessels located adjacent the spine. In some instances, the force required to penetrate the cortical bone is greater than a surgeon can apply by hand. In these instances, a hammer or other similar instrument is required to force the instrument through the cortical bone. When a hammer or similar instrument is used, there is a greater danger of the instrument passing rapidly through the cancellous bone and out the other side of the vertebra.

SUMMARY

Briefly, the invention relates to a trajectory guidance instrument that is securable to a surgical tool for use in conjunction with X-ray machines. More particularly, the device includes a radiolucent outrigger having radiodense indicia disposed on the outrigger so that the radiodense indicia is visible via a radiography, e.g. X-ray, machine to provide an angular trajectory for the instrument. The outrigger is securable to various surgical tools for the purpose of providing real time trajectory guidance to surgeons during a procedure. In general, the precision trajectory guidance instrument comprises a substantially rigid outrigger device which is securable to a portion of the surgical tool for trajectory guidance. The trajectory guidance instrument may be attached with clips, fasteners, adhesives, hook and loop or the like. Alternatively, the trajectory guidance instrument may be permanently affixed or integrally formed to the surgical tool. More than one trajectory guidance instrument may be secured to the same surgical tool, or the trajectory guidance instrument may be rotatable about the surgical tool to provide a compound angle of trajectory. Accordingly, it is an objective of the present invention to provide a trajectory guidance instrument which can be utilized to provide a precise trajectory for a surgical tool.

It is another objective of the present invention to provide a trajectory guidance instrument which can be secured to a surgical tool to provide a precise trajectory for the tool for insertion into a patient.

It is yet another objective of the present invention to provide a trajectory guidance instrument that can be secured to a pre-existing surgical tool for providing a precise trajectory for the surgical tool.

Still yet another objective of the present invention is to provide a trajectory guidance instrument that can be integrally formed as a portion of a surgical tool for providing trajectory guidance to the surgical tool.

A further objective of the present invention is to provide a trajectory guidance instrument that can be rotated with respect to the surgical tool to provide a compound angle trajectory for the surgical tool.

An even further objective of the present invention is to provide a trajectory guidance instrument particularly suited for use in spinal surgery to provide a trajectory into a vertebra with a measured angle, the measured angle and distance having been predetermined by radiography.

Still yet a further objective of the present invention is to provide a trajectory guidance instrument which can be used to ensure a desired trajectory and/or monitoring the trajectory of surgical instruments and/or implants in any number of surgical procedures, such as bone marrow biopsies, placement of spinal implants, spinal surgery, including ensuring proper placement of pedicle screws during pedicle fixation procedures and ensuring proper trajectory during the establishment of an operative corridor to a target site.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Figure 1:
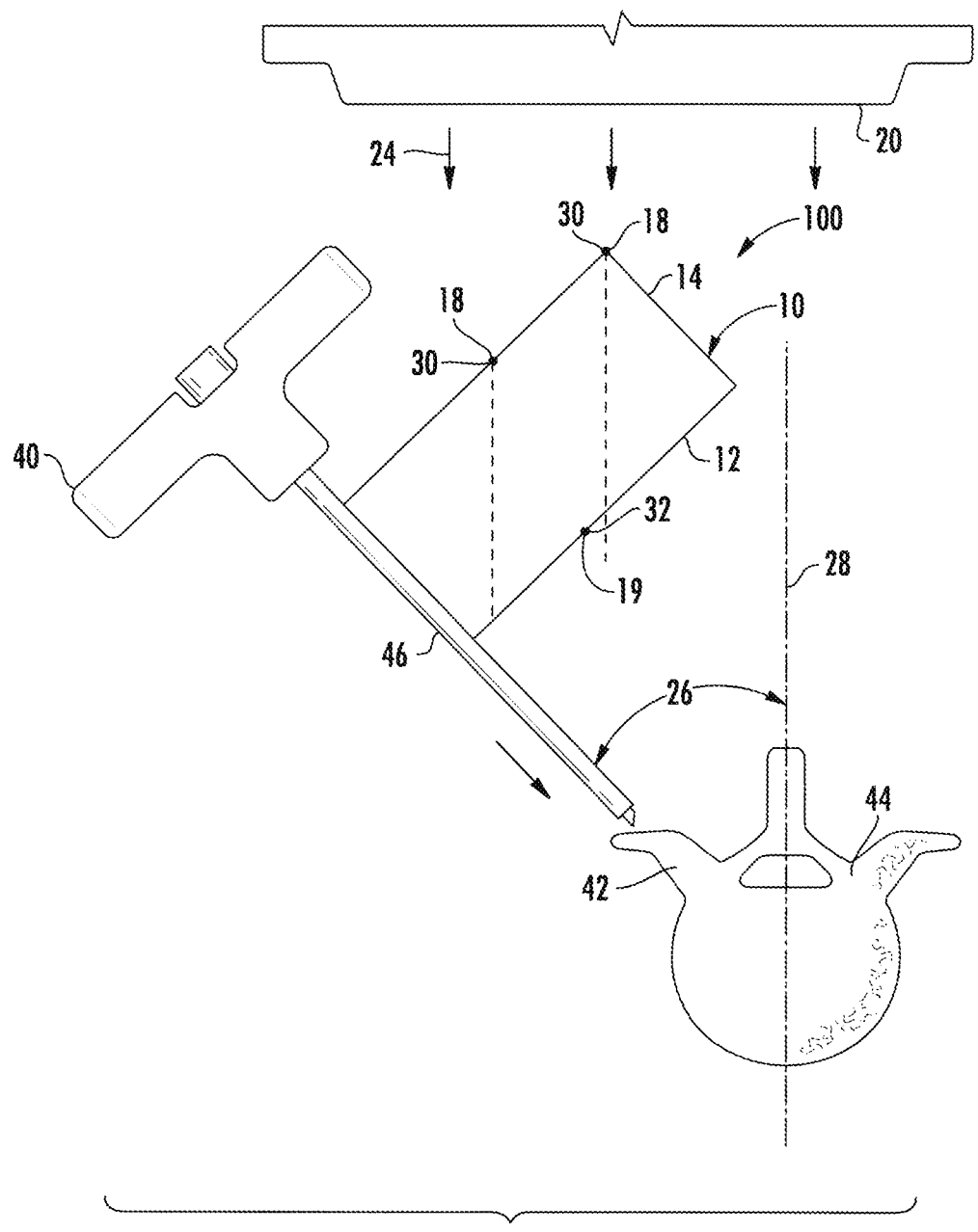
FIG. 1 is a side view of one embodiment of the instrument, illustrated with a jamshidi needle and partial view of a C-arm type x-ray device.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Various embodiments and surgical uses of a trajectory monitoring system are described for enhancing the safety and efficiency of surgical procedures. In one example, set forth by way of example only, the present invention may facilitate safe and reproducible pedicle screw placement by monitoring the axial trajectory of various surgical instruments used during pilot hole formation and/or screw insertion. In another example, set forth by way of example only, intraoperative imaging performance may be improved and radiation exposure minimized by monitoring the precise orientation of the imaging device. In yet another example, monitoring the orientation of surgical access instruments can aid in both the insertion and positioning of the access instruments themselves, as well as aiding in the later insertion of instruments and/or implants through or with the surgical access instruments. It is expressly noted that these examples are set forth by way of example; and that the present invention may be suitable for use in any number of additional surgical actions where the angular orientation or trajectory or depth (linear distance traveled) of instrumentation and/or implants is important. By way of example only, the present invention may be useful in directing, among other things, the formation of tunnels for ligament or tendon repair and the placement of facet screws. Other uses may include orientation of drills, saws, cutters or other hand operated tools used in the performance of surgery where specific fiducial markers may be useful.

Figure 2:
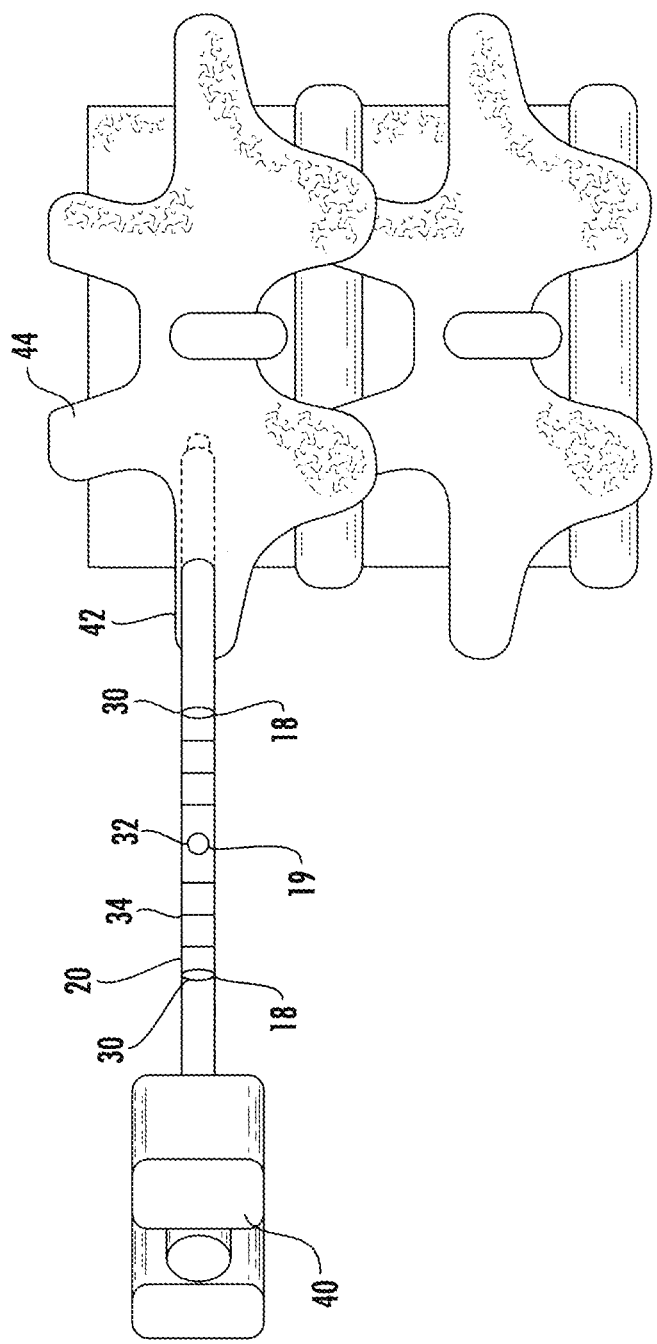
FIG. 2 is a top view of one embodiment of the instrument, illustrating the indicia under x-ray or fluoroscopy.

FIGS. 1-2, which are now referenced, illustrate one embodiment of the present invention and one manner in which it may be assembled. Like reference numerals refer to like components in the various figures. FIG. 1 is a schematic representation showing an embodiment of a precision trajectory guidance instrument 100 illustrated herein as an outrigger 10 secured to a jamshidi needle 40. The instrument 10 comprises a radiolucent body portion 14 having radiopaque indicia 18 forming a front sight 30 and a rear sight 32 which can be aligned under radiography for the purpose of preventing unintended injury to surrounding tissues, nerves, blood vessels, cartilage or bone. The visibility of the indicia 18 under radiography ensures a precise trajectory and/or monitoring of the trajectory of surgical instruments and/or implants in any number of surgical procedures, such as bone marrow biopsies, placement of spinal implants, spinal surgery, including ensuring proper placement of pedicle screws during pedicle fixation procedures, and ensuring proper trajectory during the establishment of an operative corridor to a spinal target site. A trajectory indicium 19, e.g. rear sight 32, which is also radiopaque is provided for determining an angular relationship and is aligned in a horizontal or vertical plane between the front sights 30. The indicia 18 can also include at least one reference trajectory sight 34 which indicates various degree graduations between the front sights 30. In some embodiments, the indicia 18 may be embossed, printed, painted, embedded or otherwise imprinted on a sticker, clip or outrigger. The radiopaque materials utilized for the indicia may include one of several metals known to be radiopaque such as, but not limited to, lead, tantalum, tungsten, gold, stainless steel or the like. Alternatively, the indicia may be a radiopaque polymer; such polymers are available under the trade name LATIGRAY from LATI Industries Thermoplasici S.p.A. of Italy, and may be directly adhered or molded into the outrigger.

By way of example only, while placing bone screws through a pedicle 42 (which is a small generally tubular structure connecting posterior elements of a vertebra 44 to the vertebral body), it is critical to ensure the screw is contained within the pedicle and does not breach the outer pedicle wall. Since the pedicle 42 is surrounded by delicate nervous tissue, a breach can have serious consequences for the patient, ranging from mild pain to paralysis. One way to mitigate the risk of a pedicle breach during screw placement (including preparation for screw placement, such as pilot hole formation and tapping) is to determine the angular orientation of the pedicle, and thereafter advance the necessary instruments and screws along the determined trajectory. By orienting the surgical access components along the pedicle trajectory, the surgical instruments and pedicle screws may be simply and efficiently advanced along the same trajectory, and thus avoid a breach by "eyeballing" alignment with the access components.

Thus, in spinal surgery, before the pilot hole is formed with the jamshidi 40, the desired angular trajectory must first be determined. Preoperative superior view utilizing AP fluoroscopy, MRI or CAT scan imaging device(s) 20 are used to determine the trajectory once the Jamshidi 40, in combination with the outrigger 10, has been placed at the anatomical site for which the surgery is to be conducted.

Figure 10:
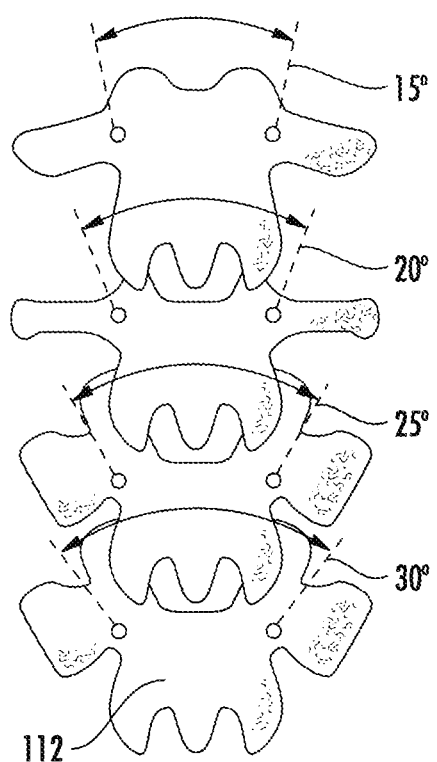
FIG. 10 is a representative illustration of a portion of the human spine.
Figure 11:
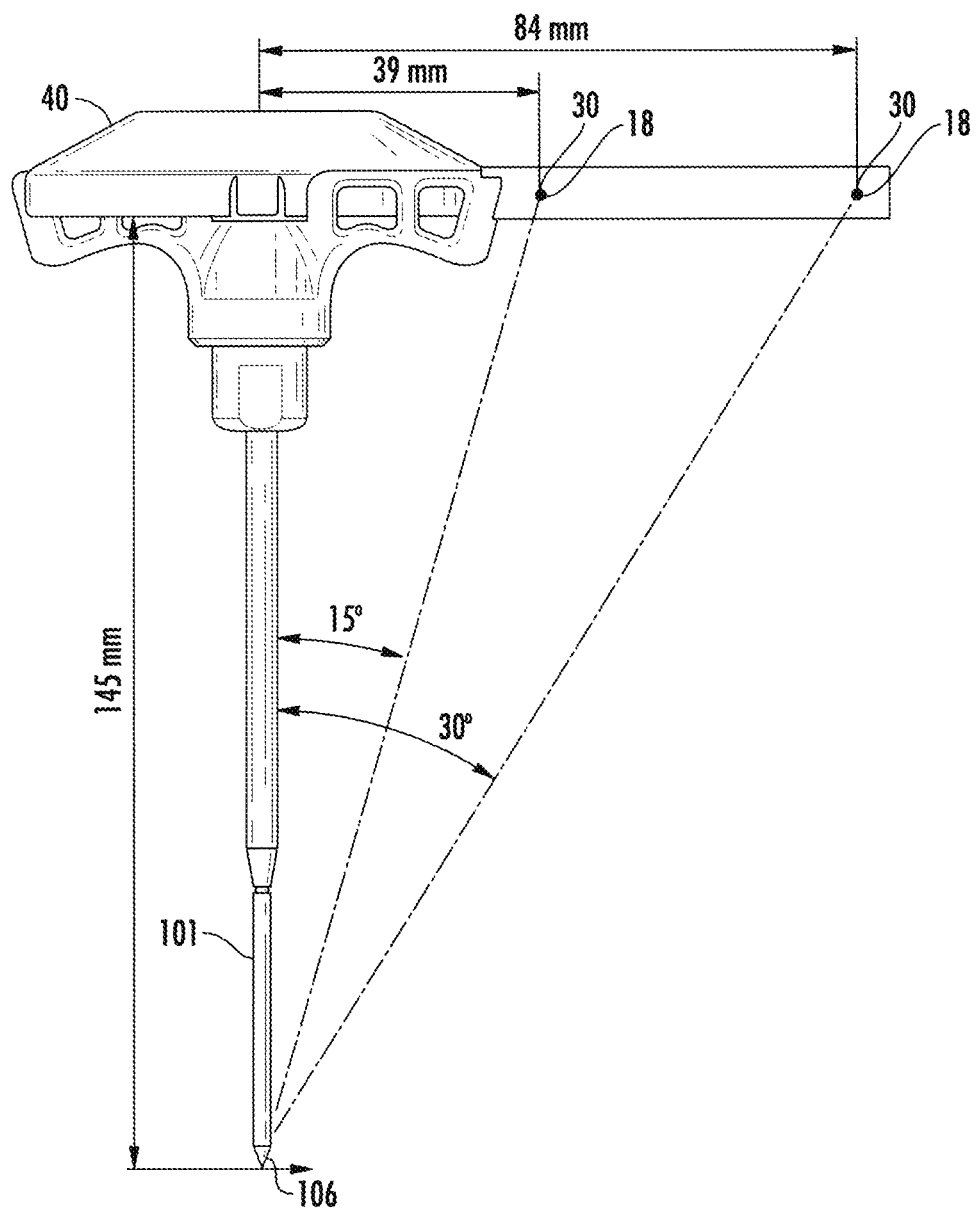
FIG. 11 is a side view illustrating one embodiment of the present invention.
Figure 12:
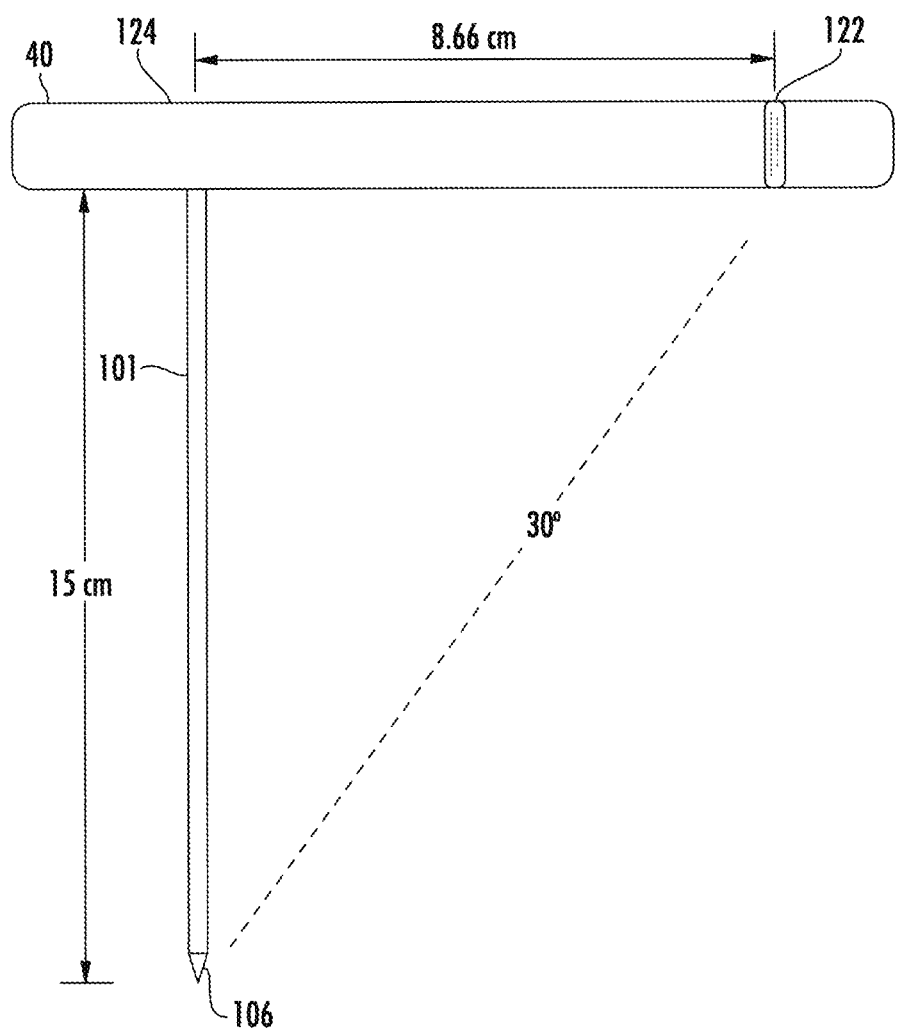
FIG. 12 is a side view illustrating one embodiment of the present invention.
Figure 13:
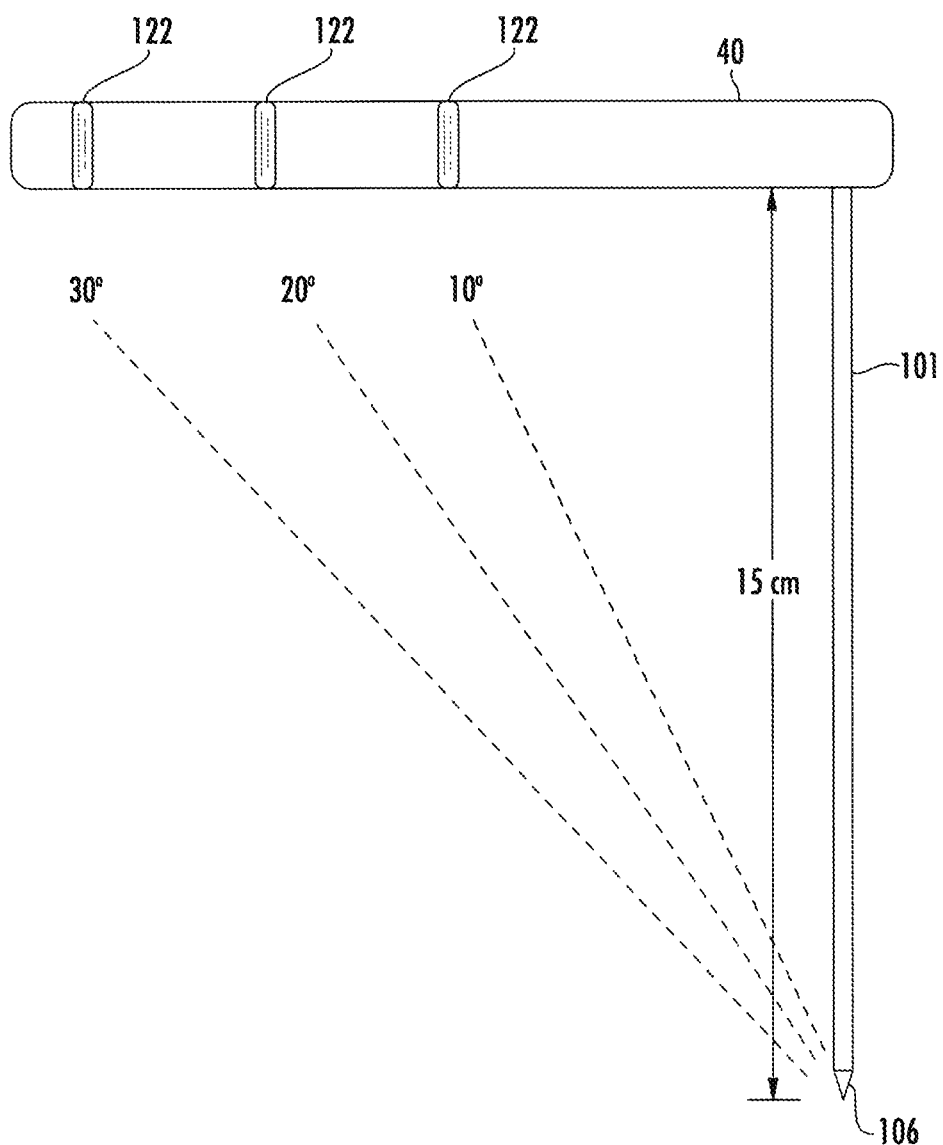
FIG. 13 is a side view illustrating one embodiment of the present invention.

C-arm fluoroscopes are used extensively during many surgical procedures. During spinal surgery for example, the C-arm is used frequently to help locate specific structures of the spine, to direct the positioning of surgical instruments and/or instrumentation, and to verify the proper alignment and height of vertebra, among other uses. Imaging devices, such as the C-arm, are typically provided with a scale (not shown) indicating the orientation of the radiography beam 24 with respect to the patient and thus, in this example, the Jamshidi 40 in combination with the outrigger 10. In this manner, the imaging device 20 can direct a radiography beam 24 across the outrigger 10 at a known angle, causing the indicia 18 to become visible in the resulting image 20 (FIG. 2). As shown in FIG. 2, the indicia 18, e.g. front sight 30 can be viewed in combination with the rear sight 32 to define the outer boundaries of the desired angle which is visible between the front sights 30. Spacing between the front sights 30 can be altered to provide any desired range of angle indication. It should also be noted that while only two front sights 30 are illustrated, any number of reference trajectory sights 34 may be provided to indicate angles or portions of angles without departing from the scope of the invention. See FIGS. 13, 15, 16 and 17 which illustrate embodiments having at least three different angular indicators. In this manner, for surgical procedures such as those to the spine wherein the coronal (medial) angle 26 increases approximately 5 degrees per level, with respect to centerline 28 from L1 to the sacrum (FIG. 10), a plurality of front sights 30 or reference trajectory sights 34 may be provided, whereby the surgeon can utilize a different front sight 30 or reference trajectory sight 34 for each level of the spine. In some embodiments, the front sights 30, rear sight(s) 32 and reference trajectory sights 34 may include different shapes including, but not limited to, numbers, letters, 2D and 3D geometric shapes and the like to indicate different angles, sights or reference sights. The indicia 18 may or may not be visible to the naked eye as the outrigger 10 is viewed. It should also be noted that while the present disclosure depicts a jamshidi needle, the teachings of the present disclosure may be applied to other types of surgical tools without departing from the scope of the invention. For example, drills, saws, reamers, shapers and other hand operated tools used for surgical operations may benefit from the teachings of the present invention. In addition, the teachings of the present invention may be utilized for the implantation of various implants, catheters, scopes and the like without departing from the scope of the invention. It should be further noted that while the outrigger 10 of the present embodiment is illustrated as being attached to the surgical tool, the teachings of the present device may also be utilized as a permanently secured or integrally formed portion of a surgical tool without departing from the scope of the invention.

Figure 3:
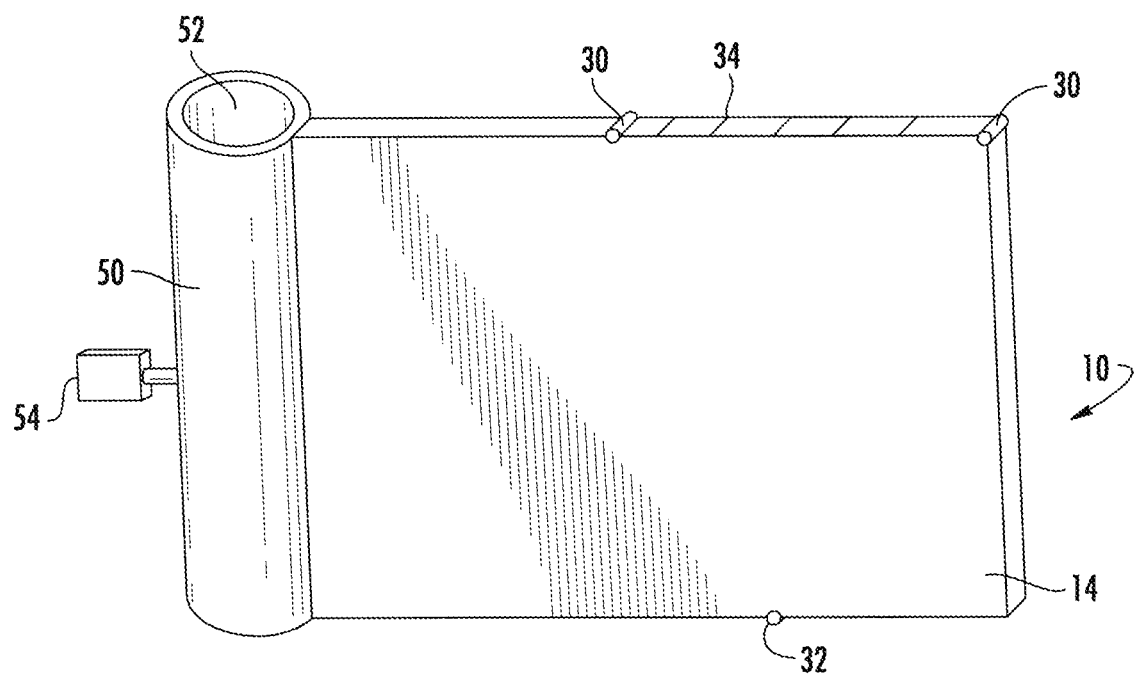
FIG. 3 is a perspective view of one embodiment of the outrigger.

Referring to FIGS. 1 and 3, one embodiment of an outrigger 10 is illustrated. In this embodiment, the radiolucent body portion 14 of the outrigger is provided with a tube portion 50 for attachment to a surgical tool such as a Jamshidi 40. The tube portion 50 includes an inner lumen 52 sized to extend around the shaft 46. Thumb screws 54, friction or the like may be utilized to hold the outrigger in place on the shaft 46 or any other portion of a surgical tool that is generally round in shape. This construction also permits the outrigger 10 to be rotated as needed about the surgical tool and additional radiography shots taken in different planes whereby compound angles and the like may be indicated by the device.

Figure 4:
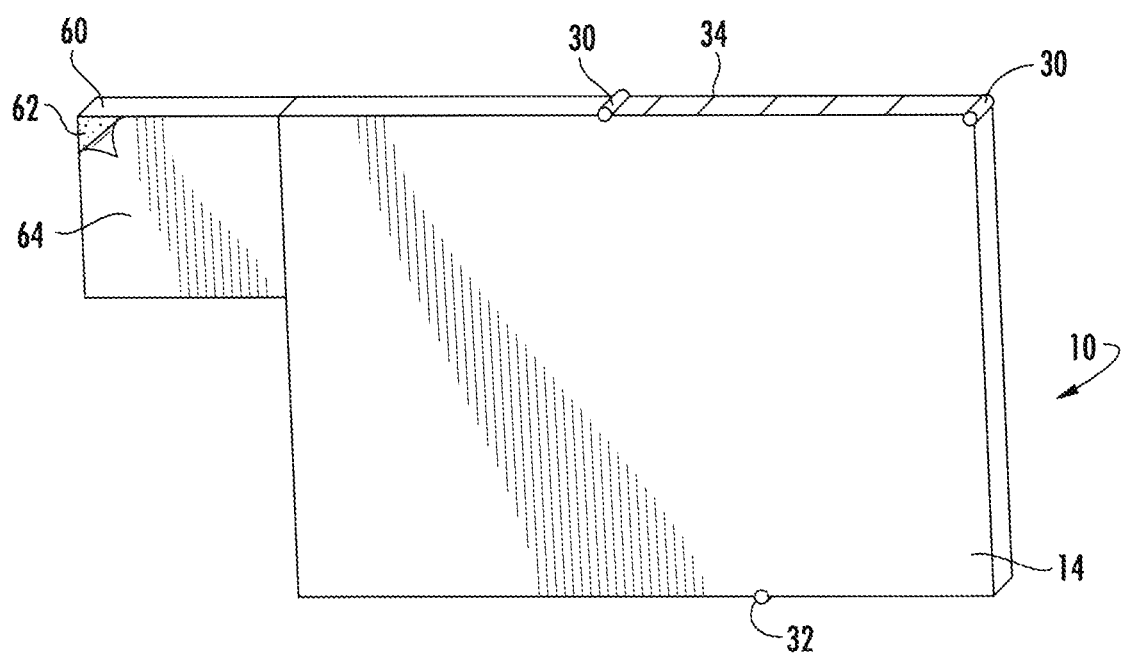
FIG. 4 is a perspective view of one embodiment of the outrigger.
Figure 5:
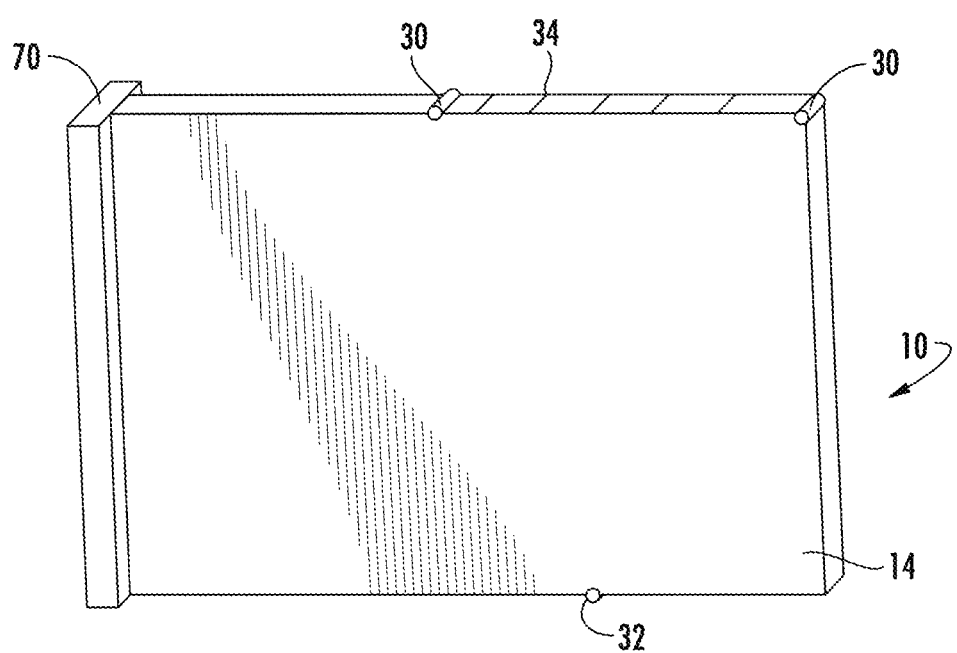
FIG. 5 is a perspective view of one embodiment of the outrigger.

Referring to FIGS. 1, 4 and 5, one embodiment of an outrigger 10 is illustrated. In this embodiment, the radiolucent body portion 14 of the outrigger is provided with a tab portion 60 or a perpendicular tab portion 70 for attachment to a surgical tool. The tab portion 60, 70 includes an adhesive 62 or the like and an adhesive cover 64 for easy attachment to a surface of a surgical tool. This construction also permits the outrigger 10 to be secured as needed to the surgical tool.

Figure 6:
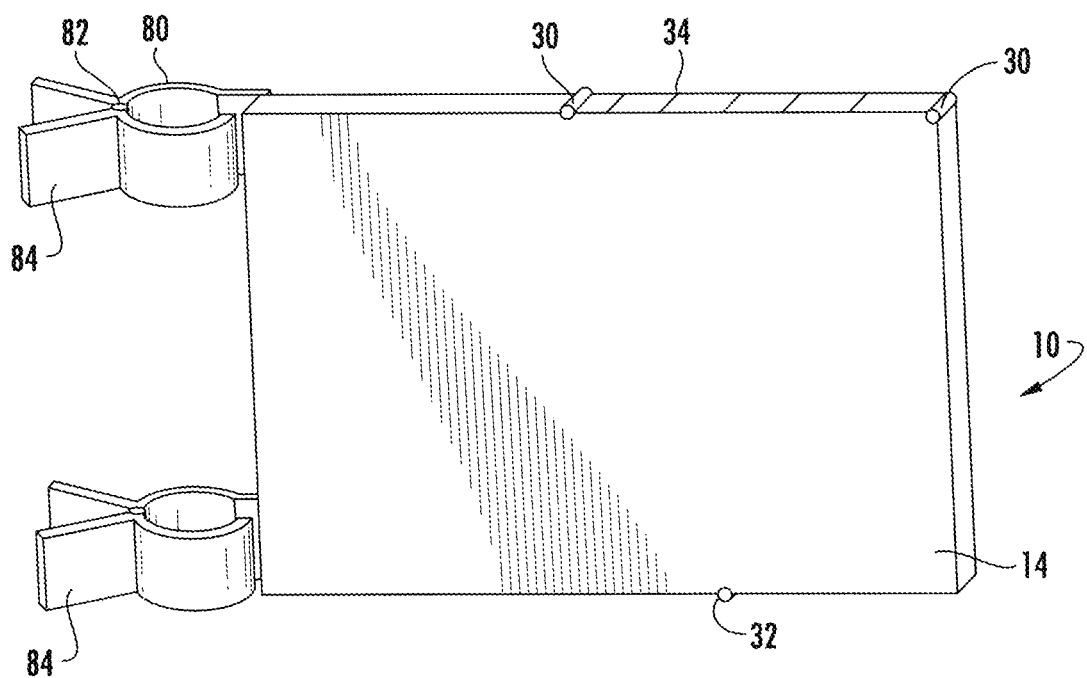
FIG. 6 is a perspective view of one embodiment of the outrigger.

Referring to FIGS. 1 and 6, one embodiment of an outrigger 10 is illustrated. In this embodiment, the radiolucent body portion 14 of the outrigger is provided with clips 80 for attachment to a surgical tool. The clips 80 include a spring member 82 or the like and a lever 84 for easy attachment to a surface of a surgical tool. This construction also permits the outrigger 10 to be secured as needed to a portion of the surgical tool in which the clip will expand large enough to fit at least partially around.

Figure 7:
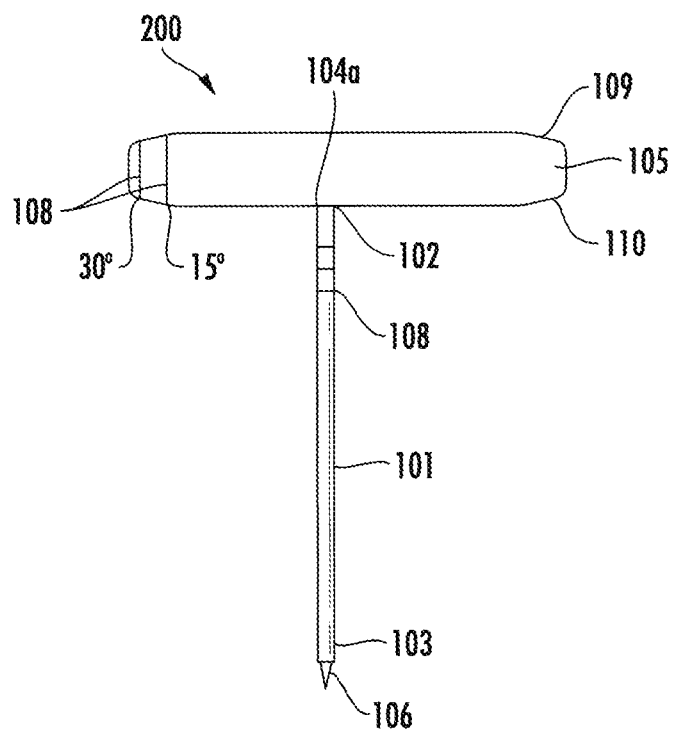
FIG. 7 is a side view of one embodiment of the present invention.
Figure 8:
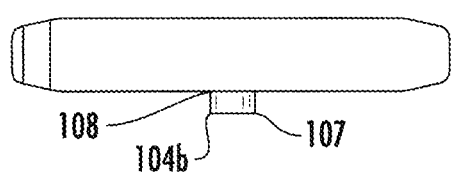
FIG. 8 is a partial view of the embodiment illustrated in FIG. 7

FIGS. 7-9, 11-14 which are now referenced, illustrate one embodiment of the present invention and the manner in which it is constructed. FIG. 7 is a schematic representation showing an embodiment of a precision depth and trajectory guidance instrument 200. The instrument 200 comprises a substantially rigid cannula 101 including a first end 102 and a second end 103, said first end including a fastener means or threaded member 104a for securing to a handle 105, said second end including a sharp tip 106 for penetrating the skin and tissue of a patient. The handle 105 is secured to the first end 102 of the cannula 101. The handle may be fixed to the cannula by various means, which include overmolding, or can be detachably removable. In embodiments where the handle 105 is detachably removable, as in FIG. 2, the handle comprises a lower portion, collar or cylindrical portion 107 including a fastener means which may include, but should not be limited to, bayonet mount, locking taper, adhesive or threaded member 104b constructed and arranged to cooperate with the fastener means or threaded member 104a of the cannula 101 for removable attachment to the cannula. This lower portion, collar or cylindrical portion 107 is fixedly secured to the cannula 101.

The handle 105 may be permanently or removably attached to the cannula 101, and may be shaped and dimensioned in any of a number of suitable variations. In some embodiments, wherein the cannula 101 is a Jamshidi-type needle, the handle 105 preferably has an ergonomic shape that can comfortably fit into a surgeon's or medical technician's hand. The handle can be shaped to include an upper curved portion 109 which is shaped to conform to an individual's palm. The lower portion of the handle 110 is also curved. The curve of the lower portion of the handle is designed to be grasped by the fingers of an individual to assist in the control of the cannula 101. The handle 105 is used to drive the cannula into, and sometimes through bones of a vertebra. Sometimes the cannula 101 can be driven through the bone only by using pressure exerted by an individual's hand. Other times a hammer or other instrument must be employed to drive the cannula 101 through a bone. There is a risk that, when a hammer or similar instrument is utilized, the Jamshidi-type cannula 101 will pass too far into a vertebra. This can cause damage to nerves located nearby. Sometimes the needle passes completely through the vertebra and injures an adjacent blood vessel or internal organ.

Figure 14:
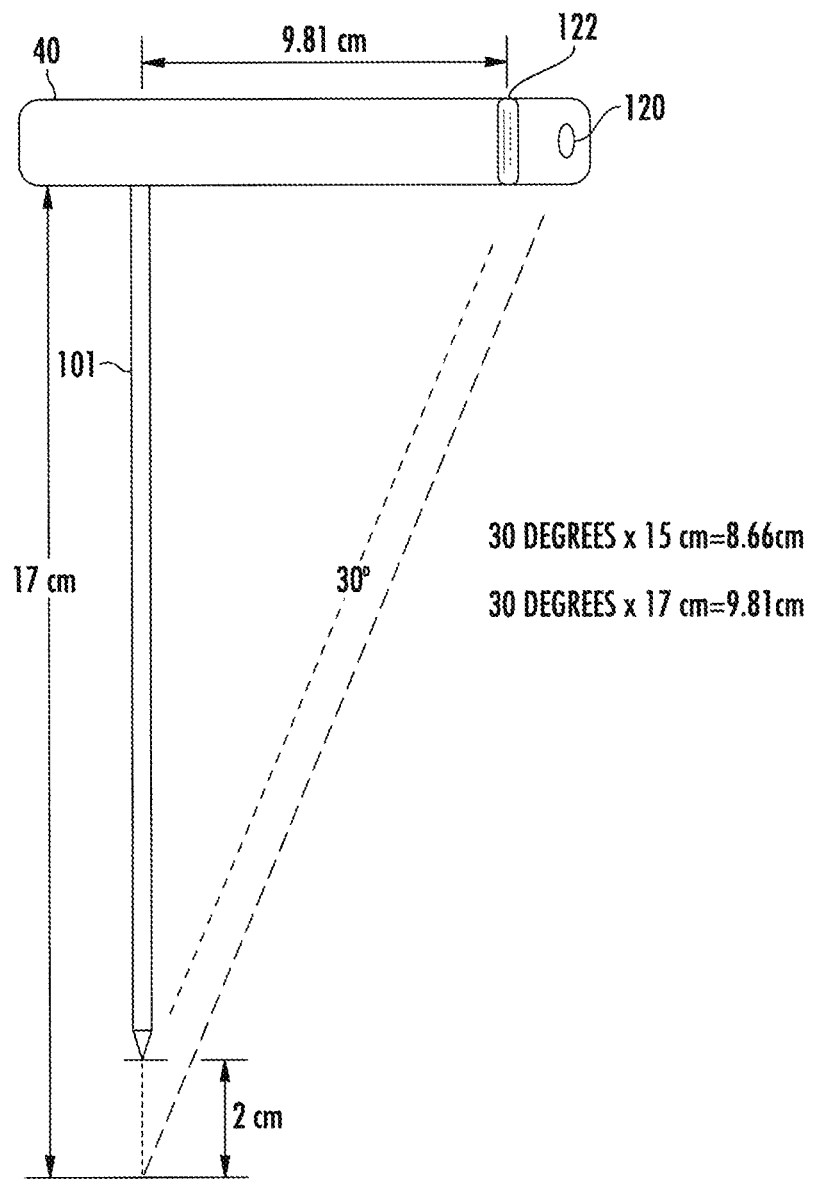
FIG. 14 is a side view illustrating one embodiment of the present invention.
Figure 15B:
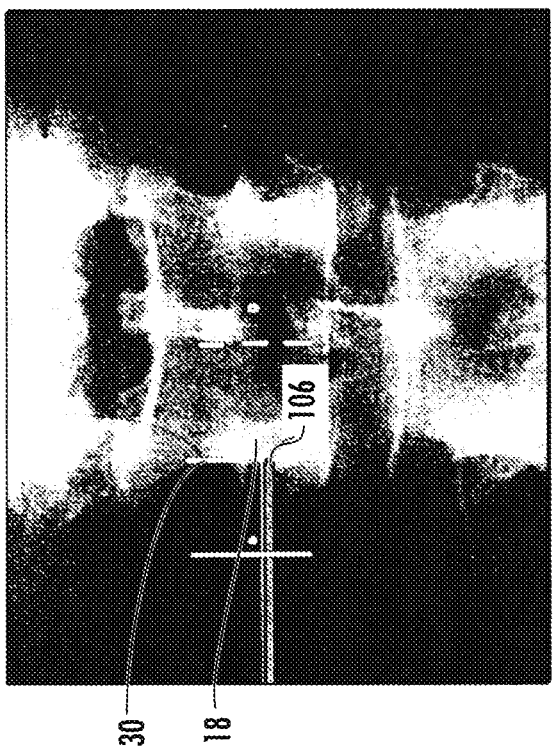
FIG. 15B is a radiographic image illustrating operation of the present invention.
Figure 15A:
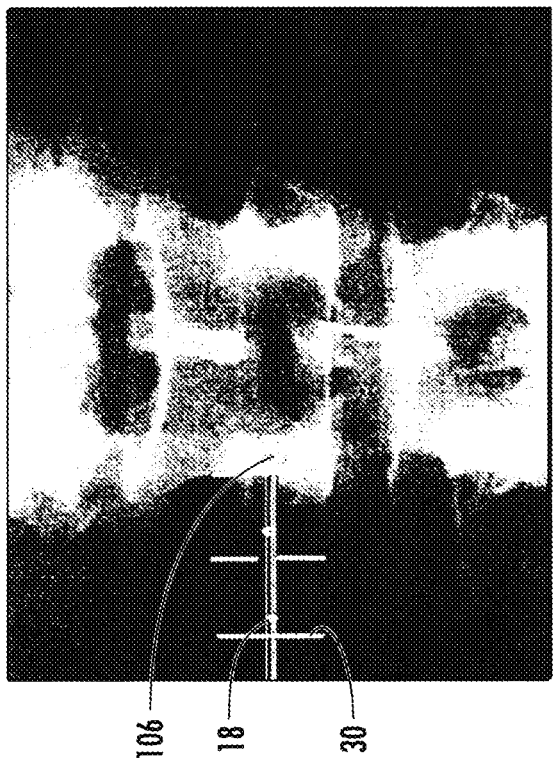
FIG. 15A is a radiographic image illustrating operation of the present invention.
Figure 15C:
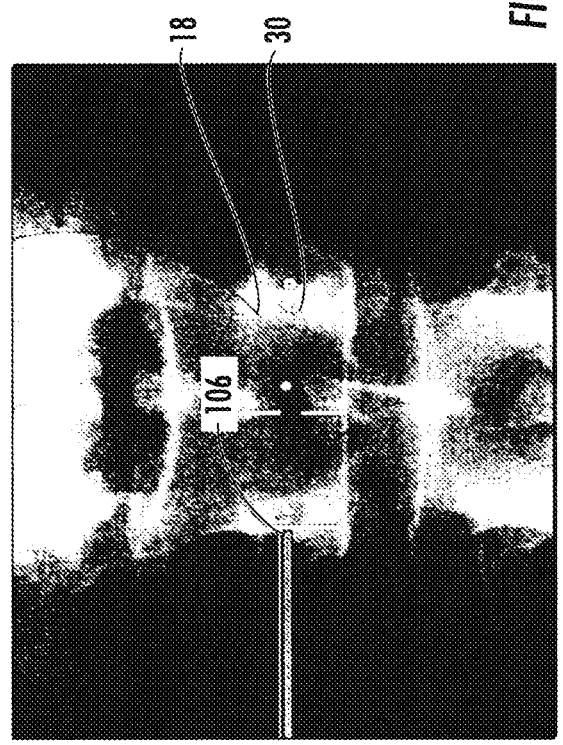
FIG. 15C is a radiographic image illustrating operation of the present invention.

For the purpose of preventing unintended injury to surrounding tissues, nerves, blood vessels, cartilage or bone, indicia 108 are disposed on the handle 105. The indicia 108 ensure a precise trajectory and/or monitoring of the trajectory and/or depth of surgical instruments and/or implants in any number of surgical procedures, such as, bone marrow biopsies, placement of spinal implants, spinal surgery, including ensuring proper placement of pedicle screws during pedicle fixation procedures, and ensuring proper trajectory during the establishment of an operative corridor to a spinal target site. A trajectory indicium for determining an angular relationship is aligned in a horizontal or vertical plane between the trajectory indicium and the sharp tip of the cannula. The indicia 108 can also include at least one reference trajectory indicium 120 (FIG. 14). The reference indicium provides a reference point or area that indicates where the tip of the tool will be if driven a predetermined distance further into the target site. In some embodiments, the indicia 108 may be embossed, printed, embedded or otherwise imprinted on a sticker or a clip. In other embodiments, the indicia are etched or electro-plated into the handle. In some embodiments, the handle includes a cutout region for accommodating attachment of a universal clip comprising indicia for trajectory and depth. It should be noted that while the present disclosure depicts a jamshidi needle, the teachings of the present disclosure may be applied to other types of surgical tools without departing from the scope of the invention. For example, drills, saws, reamers, shapers and other hand operated tools used for surgical operations may benefit from the teachings of the present invention.

Referring to FIGS. 11-14, in some embodiments the trajectory indicia comprise a 30 degree indicium, a 15 degree indicium, or combinations therebetween. In the case of a jamshidi needle, the positioning of the trajectory indicia on the surgical tool will vary according to the size of the cannula. For example, an indicium indicating a 30 degree angle 122 will be marked at 8.66 cm from the opposing end 124 of the handle of a 15 cm long cannula 101. When viewed from the top, the indicium marking the 30 degree angle 122 is aligned with the tip 106 of the cannula 101 to provide a trajectory for the surgical instrument. For a cannula having a length of 10 cm, the 30 degree indicium will be deposed at 5.77 cm from the center of the handle. Similarly, the indicia marking distance traveled are disposed on the collar and/or the cannula.

Accordingly, before the pilot hole is formed, the desired angular trajectory must first be determined. Preoperative superior view AP fluoroscopy, MRI or CAT scan images are used to determine the trajectory once the instrument has been placed at the anatomical site for which the surgery is to be conducted. A trajectory line 21 is drawn from the tip of the instrument to the appropriate indicium. The reference line is the cannula. The resulting angle between the trajectory line and the reference line is the desired angle to be used in forming the pilot hole. Alternate and/or additional methods for predetermining the pedicle angles are also contemplated and may be used without deviating from the scope of the present invention. As used herein, pilot hole formation is meant to encompass any of, or any combination of, creating a hole in a skin, tissues, bone etc. (such as, for example only, by awling, boring, drilling, etc. . . . ) and preparing a previously formed hole (such as, for example only, by tapping the hole).

Figure 9:
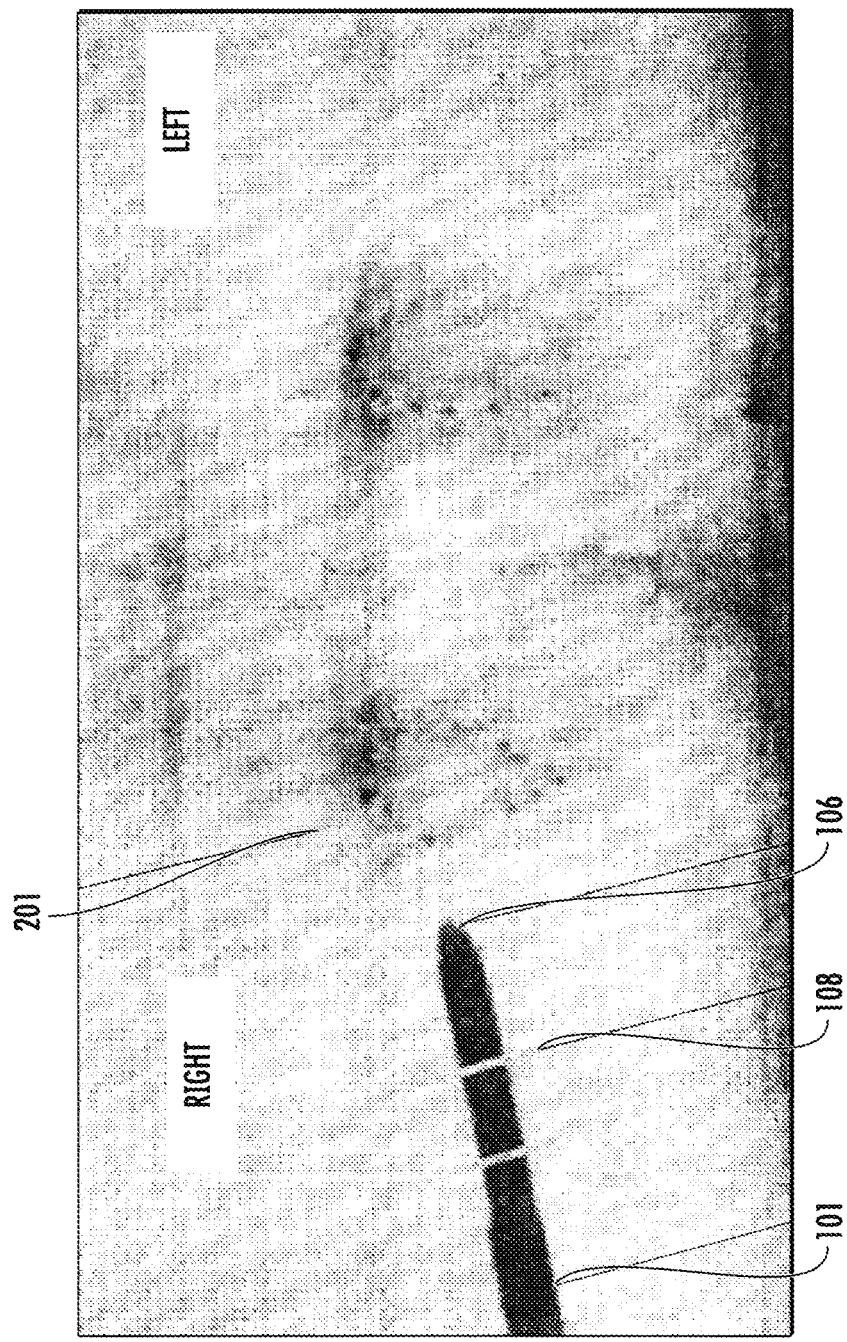
FIG. 9 is a partial radiographic view of the embodiment illustrated in FIG. 7 in operation.
Figure 16A:
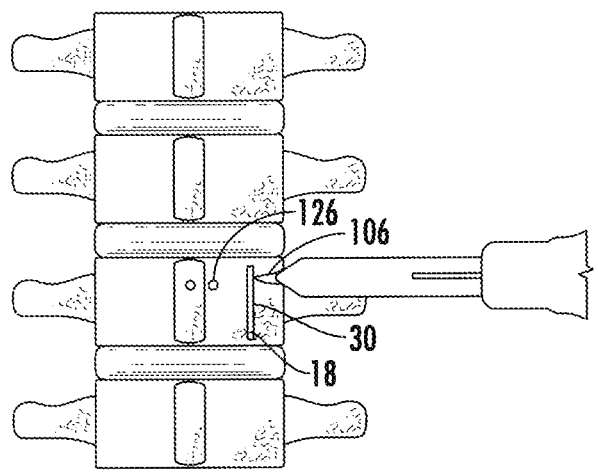
FIG. 16A is a radiographic top view image illustrating operation of one embodiment of the present invention.
Figure 16B:
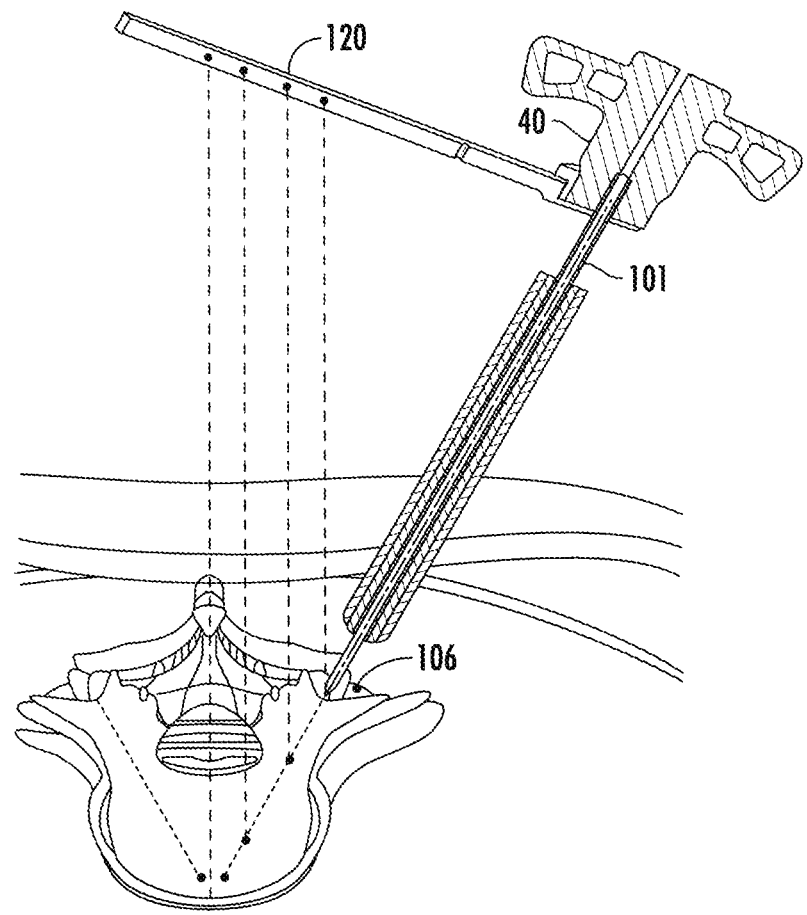
FIG. 16B is a side view illustration of the radiographic image illustrated in FIG. 16A.
Figure 17A:
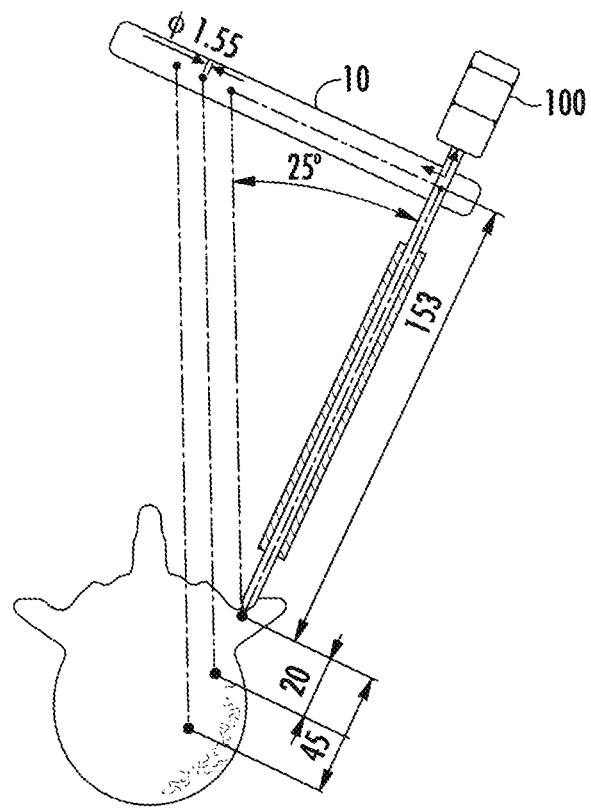
FIG. 17A is an end view illustrating operation of one embodiment of the present invention.
Figure 17B:
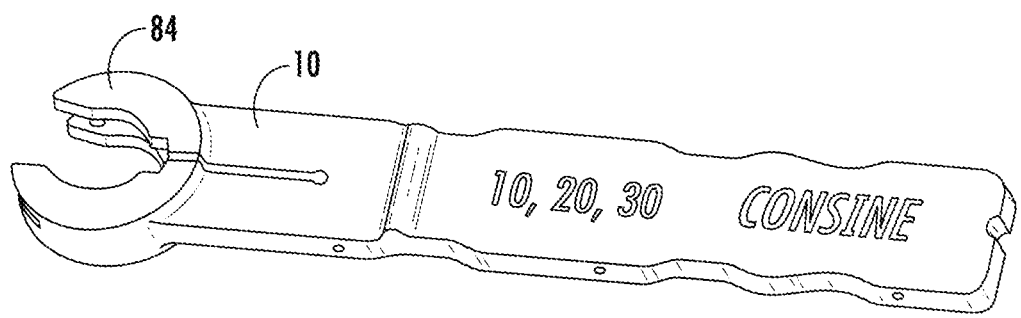
FIG. 17B is a perspective view of the embodiment illustrated in FIG. 17A.

Referring to FIGS. 9, 14-17, it is also very difficult for a surgeon or medical technician to judge the depth of penetration of a surgical instrument into the vertebra or other anatomical feature. The remedy for this problem lies in the present invention. First, the trajectory and depth instrument is placed at the anatomical site for which the surgical procedure is to occur and a radiography image of the vertebra being operated upon is taken (FIGS. 9, 16 and 17). The trajectory and depth that the surgeon wants the instrument or device to penetrate into the vertebra is thus identified prior to the surgery, allowing for an accurate surgical corridor. Accordingly, in another embodiment, a depth indicium 120 which would indicate the linear distance of the depth of the cannula is disposed into the anatomy. For example, for a projected 20 mm advance point, the depth indicium would be at 9.815 cm from the angular reference mark. (FIG. 14).

In another embodiment, a method of determining an optimal angular trajectory and linear depth for safely accessing a vertebral pedicle of a patient comprises the steps of positioning a depth and trajectory guidance instrument at a desired penetration site on a skin surface of a patient. For example, in FIG. 9, to select a starting point for pedicle 201 penetration, the instrument may be placed in the trajectory lateral position for the pedicle of interest. The instrument comprising the indicia 108 disposed on the handle and/or cannula 101 for trajectory and linear depth guidance allows for orienting the instrument along a desired trajectory by aligning the trajectory indicium with the sharp tip 106 and imaging the positioning of the instrument against the patient's anatomical image to determine an optimal surgical trajectory and depth corridor (FIG. 9).

Figure 18:
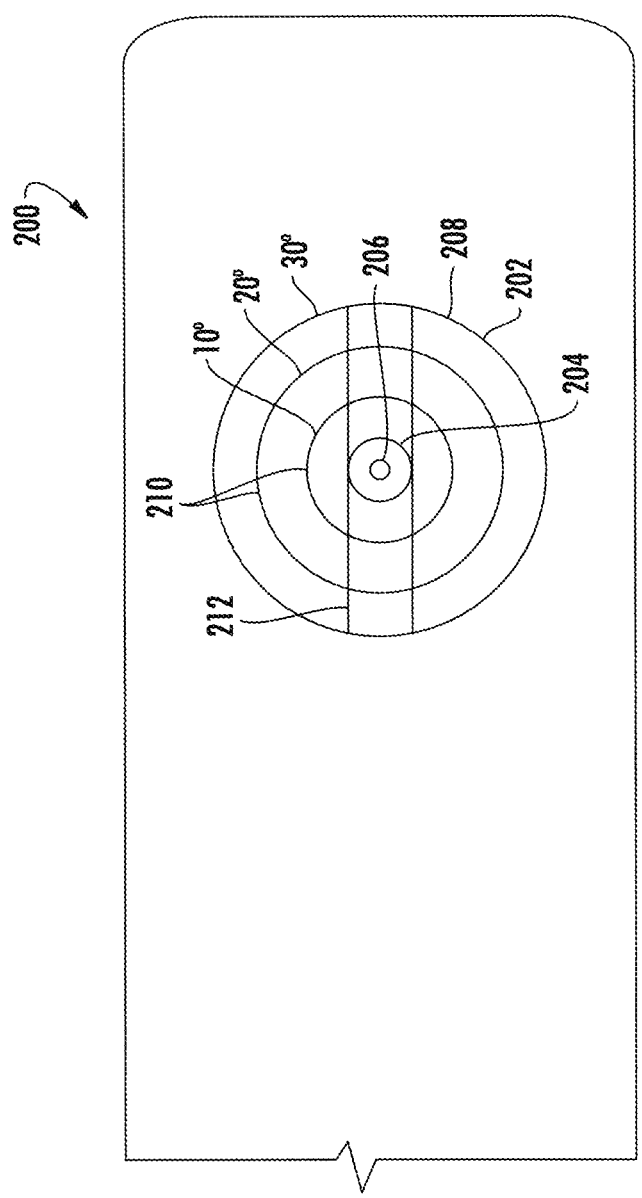
FIG. 18 is a partial perspective view of an alternative embodiment of the present invention.

Referring to FIG. 18, an alternative embodiment of the present invention is illustrated. In this embodiment, a bubble level configuration 200 of the present device may be provided which may clip onto the handle of the jamshidi, or alternatively is included within the handle, so as to ensure the instrument trajectory does not deviate during surgery and the angle is precise. The bubble level device comprises a handle with a bulls-eye level 202 mounted in it. When the handle is placed on a flat surface, an indicator ring 204 should encircle a bubble 206 captured within the glass 208. When the bubble is within the first indicator ring 204, the display should read approximately zero-degrees. Additional rings 210 would indicate the angle. For example, 10, 20 and 30 degree indicator rings 210 should encircle the bubble 206 captured within the glass. A pair of parallel lines 212 may also be provided when the bubble level is round for aligning the tool axially. In an alternative embodiment (not shown), the bubble level could be a bent elongated tube having the degree indicators printed thereon. The indicators and fluid within the level can be constructed for visualization under radiation, whereby the surgeon can read the device through the fluoroscopy or the like.

Figure 19:
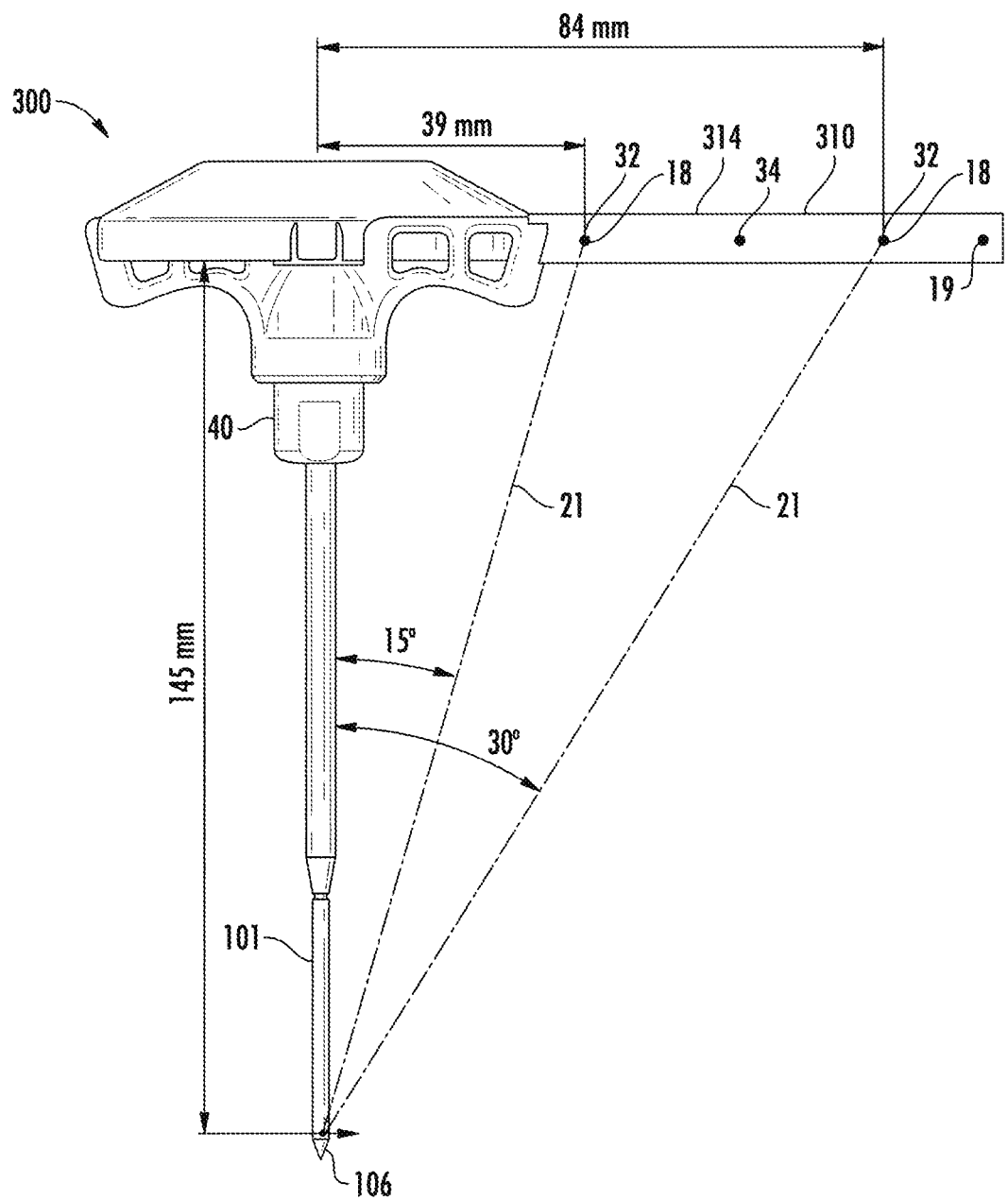
FIG. 19 is a side view of one embodiment of the present invention.

Referring to FIG. 19 an alternative embodiment of the precision guidance instrument 300 is illustrated. The precision guidance instrument 300 is illustrated herein as an outrigger 310 secured to a jamshidi needle 40. The outrigger 310 comprises a radiopaque body portion 314 having radiopaque indicia 18 forming at least one more preferably a pair of rear sights 32 which can be aligned with a portion of the surgical tool illustrated herein as the point 106 of a jamshidi needle under radiography for the purpose of preventing unintended injury to surrounding tissues, nerves, blood vessels, cartilage or bone. The visibility of the indicia 18 under radiography ensures a precise trajectory and/or monitoring of the trajectory of surgical instruments and/or implants in any number of surgical procedures, such as bone marrow biopsies, placement of spinal implants, spinal surgery, including ensuring proper placement of pedicle screws during pedicle fixation procedures and ensuring proper trajectory during the establishment of an operative corridor to a spinal target site. A trajectory indicium 19, which is also radiopaque is provided for determining the path of the surgical tool to its intended destination. The indicia 18 can also include at least one reference trajectory sight 34 which indicates various degree graduations between the front sights 30. In some embodiments, the indicia 18 may be embossed, printed, painted, embedded or otherwise imprinted on a sticker, clip or outrigger.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A precision trajectory guidance instrument for use in conjunction with a surgical tool requiring X-ray imaging for guiding said surgical tool to a surgical target site comprising: a precision trajectory guidance instrument having a radiolucent body, said radiolucent body constructed for attachment to said surgical tool at a position and orientation that causes X-rays associated with said X-ray imaging to pass through said radiolucent body at a known angle, said radiolucent body including at least one front sight constructed from a radiopaque material and at least one rear sight constructed from a radiopaque material, said at least one front sight and said at least one rear sight positioned on said radiolucent body to provide an angular relationship of said radiolucent body, and thus an angular trajectory of said surgical tool with respect to a portion of an animal anatomy in an X-ray image, wherein said surgical tool is a jamshidi needle, said precision trajectory guidance instrument secured to said jamshidi needle as an outrigger extending outwardly and generally perpendicular from a cannula portion of said jamshidi needle.

2. The precision trajectory guidance instrument of claim 1 including a plurality of said rear sights, whereby said plurality of said rear sights are aligned with said at least one front sight to provide an axial alignment and an angular alignment of said tool with respect to a portion of an animal anatomy viewable in said X-ray image.

3. The precision trajectory guidance instrument of claim 2 wherein said rear sights each include a different geometric shape.

4. The precision trajectory guidance instrument of claim 1 wherein a spacing between said plurality of said rear sights is configured to provide a predetermined range of angular indication.

5. The precision trajectory guidance instrument of claim 4 wherein said plurality of rear sights are spaced to provide a reference trajectory sight for at least two levels of the lumbar spine.

6. The precision trajectory guidance instrument of claim 1 wherein said radiolucent body of said outrigger is provided with a tube portion, said tube portion having an inner lumen sized to extend around a lumen of said jamshidi needle.

7. The precision trajectory guidance instrument of claim 6 wherein said outrigger is rotatable about said lumen.

8. The precision trajectory guidance instrument of claim 1 wherein said radiolucent body of said outrigger is provided with clips for attachment to said jamshidi needle.

9. The precision trajectory guidance instrument of claim 1 wherein said radiolucent body portion of said outrigger is provided with a tab portion, said tab portion including an adhesive for attachment to said jamshidi needle.

10. The precision trajectory guidance instrument of claim 1 wherein said surgical tool is a jamshidi needle, said precision trajectory guidance instrument integrally formed as a portion of said jamshidi needle.

11. The precision trajectory guidance instrument of claim 1 wherein said precision trajectory guidance instrument is integrally formed as an outrigger extending outwardly and generally perpendicular from a hand grip portion of said jamshidi needle.

12. The precision trajectory guidance instrument of claim 1 wherein said precision trajectory guidance instrument is integrally formed as an outrigger extending outwardly and generally perpendicular from a cannula portion of said jamshidi needle.

13. The precision trajectory guidance instrument of claim 1 including at least one depth sight secured along the length of said cannula.

14. A precision trajectory guidance instrument comprising: a surgical tool including a substantially rigid cannula including a first end and a second end, said first end secured to a handle member, said second end including a sharp tip for penetrating the skin and tissue of an animal a radiolucent body, a radiolucent body secured to said surgical tool, said radiolucent body secured to said surgical tool at a position and orientation that causes X-rays associated with said X-ray imaging to pass through said radiolucent body at a known angle, said radiolucent body including at least one front sight constructed from a radiopaque material and at least one rear sight constructed from a radiopaque material, said at least one front sight and said at least one rear sight positioned on said radiolucent body to provide an angular relationship of said radiolucent body and thus an angular trajectory of said surgical tool with respect to a portion of an animal anatomy in an X-ray image, wherein said surgical tool is a jamshidi needle, said precision trajectory guidance instrument secured to said jamshidi needle as an outrigger extending outwardly and generally perpendicular from a cannula portion of said jamshidi needle.

15. The precision trajectory guidance instrument of claim 14 wherein said radiolucent body is secured to said cannula.

16. The precision trajectory guidance instrument of claim 14 wherein said radiolucent body is secured to said handle member.

17. The precision trajectory guidance instrument of claim 14 wherein said handle is removable from said cannula.

18. The precision trajectory guidance instrument of claim 14 wherein said radiolucent body is integrally formed as part of said surgical tool.

19. The precision trajectory guidance instrument of claim 14 wherein said radiolucent body includes a plurality of said rear sights, whereby said plurality of said rear sights are spaced apart with respect to each other to provide a predetermined range of angular indication when aligned with said at least one front sight with respect to a portion of an animal anatomy viewable in said X-ray image.

20. A precision trajectory guidance instrument for use in conjunction with a surgical tool requiring X-ray imaging for guiding said surgical tool to a surgical target site comprising: a precision trajectory guidance instrument having a body, said body constructed for attachment to said surgical tool at a position and orientation that causes X-rays associated with said X-ray imaging to pass through said body at a known angle, said body including at least one front sight constructed from a radiopaque material and at least one rear sight constructed from a radiopaque material, said at least one front sight and said at least one rear sight positioned on said body to provide an angular relationship of said body and thus an angular trajectory of said surgical tool with respect to a portion of an animal anatomy in an X-ray image, wherein said surgical tool is a jamshidi needle, said precision trajectory guidance instrument secured to said jamshidi needle as an outrigger extending outwardly and generally perpendicular from a cannula portion of said jamshidi needle.

21. The precision trajectory guidance instrument of claim 20 wherein said body is formed from a radiopaque material.

22. The precision trajectory guidance instrument of claim 20 wherein said body is formed from a radiolucent material.

23. The precision trajectory guidance instrument of claim 20 wherein said body is formed from a combination of radiopaque and radiolucent materials.

24. The precision trajectory guidance instrument of claim 20 wherein said front sight is a portion of said surgical tool.

25. The precision trajectory guidance instrument of claim 20 wherein said rear sight is a portion of said surgical tool.

26. The precision trajectory guidance instrument of claim 20 wherein said front sight and said rear sight are formed as portions of said surgical tool.

27. The precision trajectory guidance instrument of claim 26 wherein said surgical tool is a jamshidi needle.

28. The precision trajectory guidance instrument of claim 27 wherein said front sight is the pointed tip of said jamshidi needle.

* * * * *